(12) United States Patent
Lawton et al.

(10) Patent No.: US 7,806,912 B2
(45) Date of Patent: Oct. 5, 2010

(54) TRANSVERSE ROD CONNECTOR

(75) Inventors: Laurence Lawton, Vista, CA (US); Thomas Purcell, Del Mar, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 734 days.

(21) Appl. No.: 11/544,893

(22) Filed: Oct. 6, 2006
(Under 37 CFR 1.47)

(65) Prior Publication Data
US 2008/0082112 A1 Apr. 3, 2008

Related U.S. Application Data

(60) Provisional application No. 60/725,031, filed on Oct. 7, 2005.

(51) Int. Cl.
*A61B 17/70* (2006.01)
(52) U.S. Cl. ........................ 606/250; 606/260
(58) Field of Classification Search ................ 606/103, 606/150–158, 250–280, 61, 246
See application file for complete search history.

(56) References Cited

U.S. PATENT DOCUMENTS

| | | | |
|---|---|---|---|
| 5,611,800 A | 3/1997 | Davis et al. | 606/61 |
| 6,569,164 B1* | 5/2003 | Assaker et al. | 606/250 |
| 2002/0111625 A1 | 8/2002 | Richelsoph et al. | 606/61 |
| 2002/0169448 A1 | 11/2002 | Vanacker | 606/61 |
| 2003/0018334 A1* | 1/2003 | Richelsoph et al. | 606/61 |
| 2006/0058789 A1* | 3/2006 | Kim et al. | 606/61 |
| 2008/0082112 A1* | 4/2008 | Lawton et al. | 606/151 |

FOREIGN PATENT DOCUMENTS

| | | |
|---|---|---|
| EP | 1 302 169 A1 | 4/2003 |
| WO | WO03-026520 | 4/2003 |
| WO | WO 03/026520 A1 | 4/2003 |

OTHER PUBLICATIONS

International Search Report dated Feb. 2, 2007.
Written Opinion dated Oct. 7, 2005.

* cited by examiner

*Primary Examiner*—Eduardo C Robert
*Assistant Examiner*—Christina Negrelli
(74) *Attorney, Agent, or Firm*—Michael R. Shevlin

(57) ABSTRACT

Embodiments of the present invention are directed to bone alignment rod connectors, and more particularly to traverse rod connectors. In one embodiment, the connector includes a housing having an opening configured to accommodate at least one rod, a setscrew assembly configured to secure the at least one rod when the at least one rod is placed in the opening. The setscrew assembly includes a setscrew and at least one circular/spherical object configured to interact with the setscrew when the setscrew is inserted in the housing. Upon insertion of the setscrew, the at least one spherical object is configured to laterally move towards the at least one rod to secure the at least one rod inside the housing.

20 Claims, 4 Drawing Sheets

TRANSVERSE ROD CONNECTOR

CROSS-REFERENCE TO RELATED APPLICATIONS

The present application claims priority to U.S. Provisional Application No. 60/725,031, to Laurence et al., filed Oct. 7, 2005, and titled "Transverse Rod Connector" and incorporates its entire disclosure herein by reference.

BACKGROUND OF THE INVENTION

1. Field of the Invention

The present invention relates generally to the field of surgery, and more specifically, to connector devices for connecting and maintaining a spaced apart relationship between bone alignment rods ("transverse rod connectors").

2. Background of the Invention

Anterior internal fixation of the thoracic and thoracolumbar spine is a growing trend in spinal surgery. In the thoracic and thoracolumbar spine, anterior fixation is indicated for burst fractures with significant canal compromise, vertebral body tumors requiring corpectomy and other indications requiring anterior stabilization. One of the advantages of anterior internal fixation includes an ability to provide complete canal clearance and decompression of bony fragments and/or total resection of a tumor. Additionally, anterior thoracic and thoracolumbar (ATL) surgery allows for fusion of a minimal number of motion segments, thus, allowing for more normal spine mechanics.

Some conventional systems relate to a design of a rod-based system primarily for the management of thoracic, thoracolumbar, and lumbar burst fractures and tumors that permits anterior load sharing, allows for distraction to perform reduction and compression of the bone graft, is CT/MRI compatible, and easy to implant. Conventional systems can include vertebral body staples, plates, and anterior instruments used in conjunction with a variety of screws and rods to create a high-versatile anterior fixation system.

Some conventional systems further include titanium construction that is compatible with current CT and MRI scanning technology, low profile implant systems, top-loading and top-tightening systems, and other parameters. Some systems also include cross-connectors that allow one-piece implant to be applied to a dual-rod construct for a top-loading approach.

The conventional devices and systems have a number of disadvantages. These devices do not provide flexibility when adjusting the devices either prior to, during, or after their placement into the patient. Thus, these devices force a surgeon to utilize a specific configuration, leaving very little room for adjustment in accordance with patient's physiological characteristics and needs. Further, these devices do not allow a surgeon to connect multiple rods by actuating a single setscrew mechanism.

Thus, there is a need for a fixation device that will provide flexibility to a surgeon or other qualified professional when installing and adjusting this fixation device to a particular patient as well as an ability to secure multiple rods of the device.

SUMMARY OF THE INVENTION

Some of the embodiments of the present invention are directed to rod connectors, and more particularly to transverse rod connectors configured to secure multiple rods using, for example, a single setscrew.

In one embodiment, the connector includes a bone alignment rod connector including a housing having an opening configured to accommodate at least one rod and a setscrew assembly having a setscrew and at least one circular object/member configured to interact with the setscrew when the setscrew is inserted in the housing. The setscrew assembly is configured to secure the at least one rod when the at least one rod is placed in the opening and upon insertion of the setscrew, the at least one circular object is configured to laterally move towards the at least one rod to secure the at least one rod inside the housing.

In another embodiment, a method for securing a bone alignment rod within a receiving portion of a housing includes providing a housing having a receiving portion for receiving a bone alignment rod, a setscrew, and a top threaded opening configured to receive the setscrew and allow the setscrew to advance therein to establish a retaining force to retain the bone alignment rod within the receiving portion. The method also includes receiving the bone alignment rod within the receiving portion of the housing and advancing the setscrew into the threaded opening to establish the retaining force to retain the rod within the receiving portion.

In yet another embodiment, a method for securing a spaced apart relationship between two bone alignment rods includes providing a housing having a pair of receiving portions in a spaced apart arrangement and each for receiving a respective bone alignment rod, a setscrew, and a top threaded opening configured to receive the setscrew and allow the setscrew to advance therein to establish a retaining force to retain each bone alignment rod with a respective receiving portion. The method also includes receiving a respective bone alignment rod within each receiving portion of the housing and advancing the setscrew into the threaded opening to establish the retaining force to retain each bone alignment rod in a respective receiving portion.

Other embodiments of the present invention may be used to connect two rods (or more), preferably rigidly and preferably simultaneously, by actuating a single setscrew, and maintaining the rods in a spaced apart arrangement. Specifically, some embodiments of the invention include a main body having two slots (receiving portions), each sized appropriately to accommodate a rod in use and which are substantially parallel (for example). The main body may also include a hole having an axis which is substantially perpendicular to an axis of one or preferably both of the rod slots, and a third slot extending laterally on either side of the hole towards the two slots.

The setscrew may have a conical surface (or other surface, e.g., spherical) on the interior portion to directly actuate the spheres against the rods. The setscrew may also indirectly actuate the spheres/circular members by using an insert with a relieved portion to accommodate the setscrew. The insert preferably includes an inclined surface at the sphere contact portion to facilitate actuation of the spheres. The forces that force a sphere outward may also tend to deform the insert against the setscrew. Thus, increased rotational force on the setscrew is transformed into a setscrew gripping action by the insert itself. This gripping action may prevent the setscrew from loosening during dynamic loading conditions (for example).

The rod slots may be oversized to accommodate the capturing of rods which are initially skewed. Accordingly, in one embodiment of the invention, the action of tightening the setscrew captures the rods and persuades the rods into a substantially parallel configuration (for example) —this is accomplished by forcing the rods against a lateral surface of the rod slot. The openings of the lateral slot at the bilateral rod slots may be smaller than the space in which the spheres translate in order to prevent expulsion of the spheres from the interior body.

Further features and advantages of the invention, as well as structure and operation of various embodiments of the invention, are further elaborated in detail below with references to the accompanying drawings.

BRIEF DESCRIPTION OF THE DRAWINGS

The present invention is described with reference to the accompanying drawings. In the drawings, like reference numbers indicate identical or functionally similar elements. Additionally, the left-most digit(s) of a reference number identifies the figure number drawing in which the reference number first appears.

DETAILED DESCRIPTION OF THE INVENTION

Some embodiments of the present invention relates to the field of surgery, and more specifically to a bone alignment rod (e.g. transverse rod) connector that may hold at least one and preferably two (or more) rods. The rod can be a cervical rod, a posterior rod, or any other rod used during medical applications.

Figure 1:
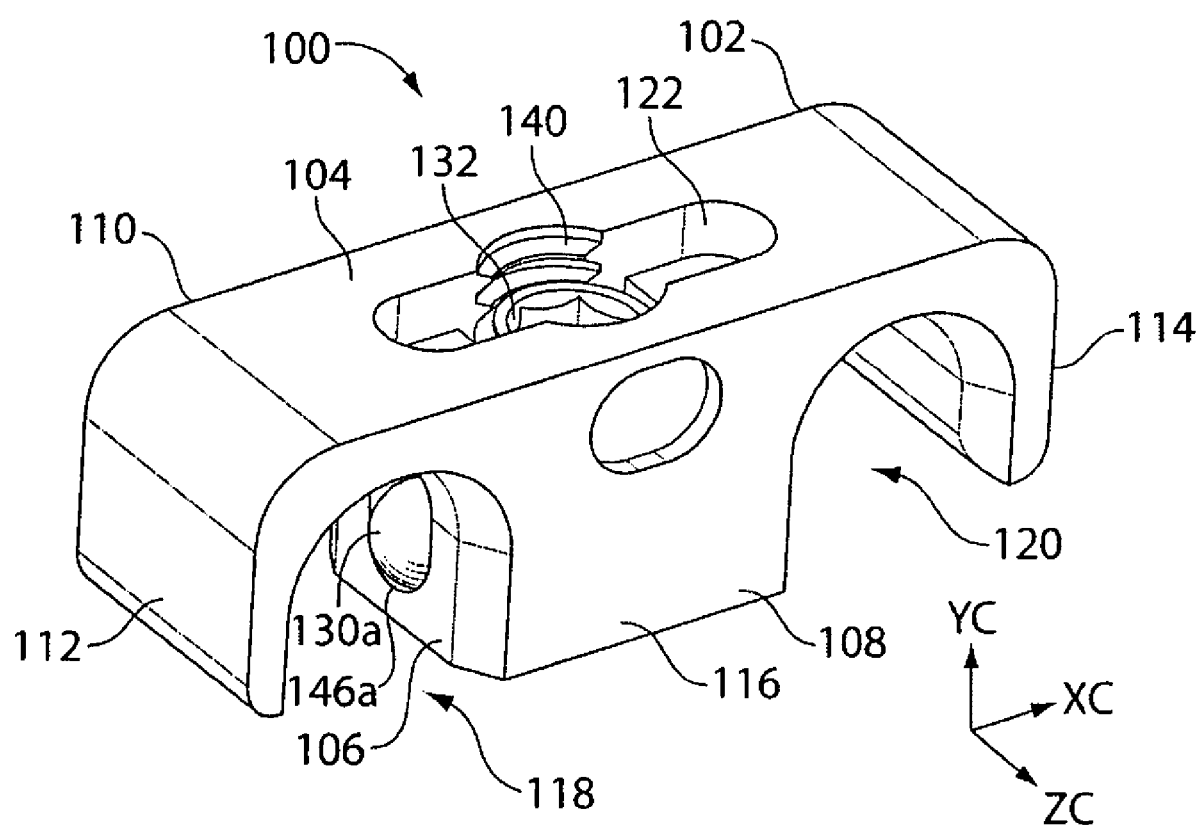
FIG. 1 illustrates a perspective view of a lateral slot configuration according to one embodiment of the present invention (indirect actuation with lateral insert).

FIG. 1 illustrates a perspective view of the transverse rod connector 100, having a housing 102 which includes a top portion 104, a bottom portion 106, a front portion 108, a back portion 110, and side portions 112, 114. As illustrated, an x-y-z coordinate system can be used to better visualize the spatial orientation of elements in the housing 102. Accordingly, the top and bottom portions 104, 106 are disposed in an x-z coordinate field, the side portions 112, 114 are disposed in the y-z coordinate field, and the front and back portions 108, 110 are disposed in the x-y coordinate field.

The housing 102 further includes a central portion 116, which, in the presently illustrated (FIG. 1) embodiment, is disposed substantially in the middle of the housing 102. The housing 102 further includes two open channels or openings 118, 120 disposed between the two side portions 112, 114 and the central portion 116. The open channels 118, 120 may be formed by the top portion 104 and two side portions 112, 114 in the x-z coordinate field, and the central portion 116 in the y-z coordinate field. Thus, the open channel 118 is formed by the side portion 112, central portion 116 and the top portion 104. The open channel 120 is similarly formed by the side portion 114, central portion 116 and the top portion 104. The open channels 118, 120 may be open from the bottom portion 106 of the housing 102. As can be understood by one skilled in the art, the housing 102 can include at least one such opening configured to accommodate placement of at least one rod.

In the illustrated embodiment, the openings 108, 110 are configured to accommodate cylindrical rods, although, as can be understood by one skilled in the art, the openings 108, 110 can accommodate any shape rods, and may be formed to accommodate specially, custom shaped rods.

The top portion 104 may further include an opening 122, which may be elliptical, having a first, shorter diameter along the z-axis and a second, longer diameter along the x-axis. As can be understood by one skilled in the art, the opening 122 can have any other desired shape, such as circle, rectangle, square, polygon, or any other shape.

Figure 2:
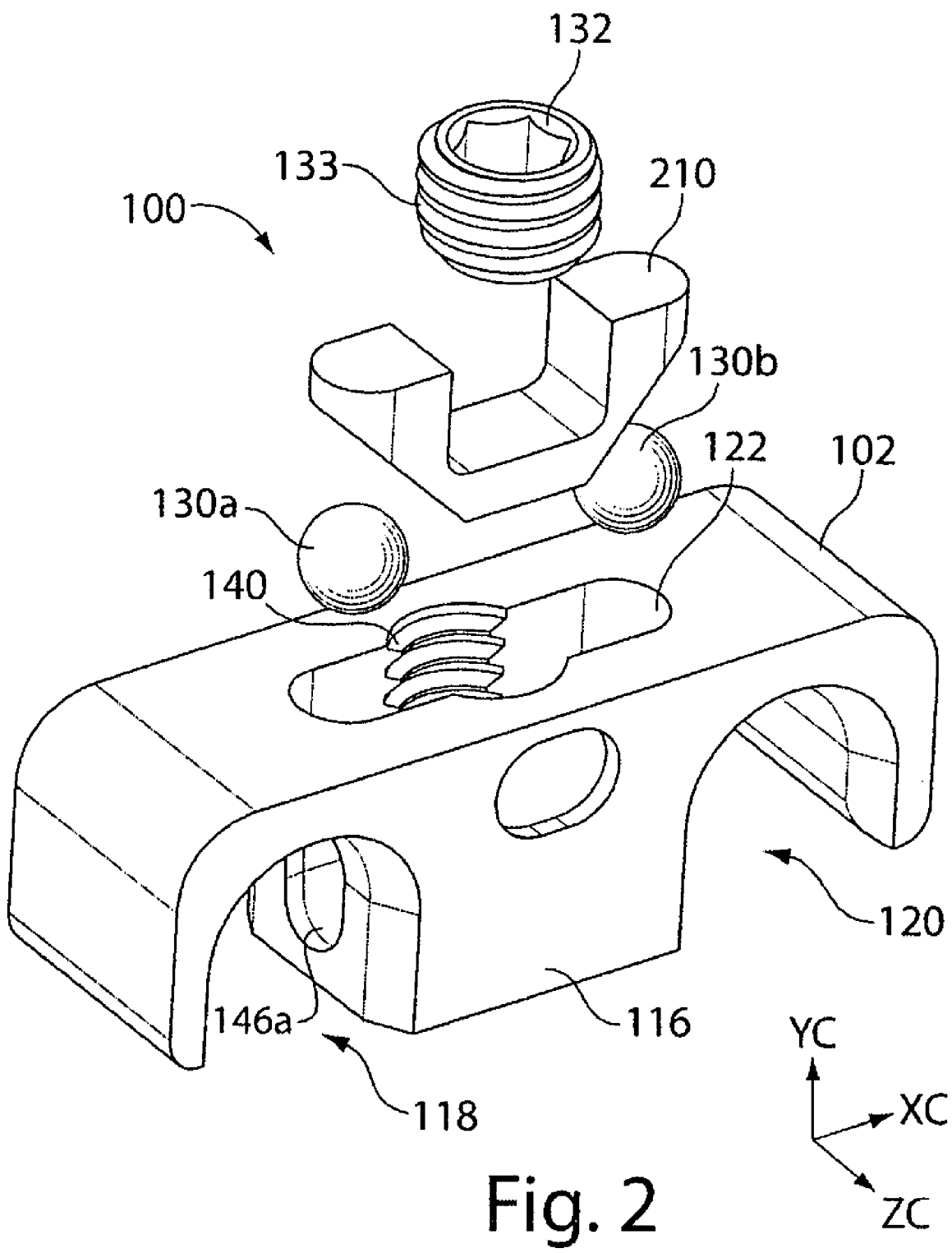
FIG. 2 illustrates an exploded, perspective view of a lateral slot configuration according to one embodiment of the present invention (indirect actuation with lateral insert).
Figure 3:
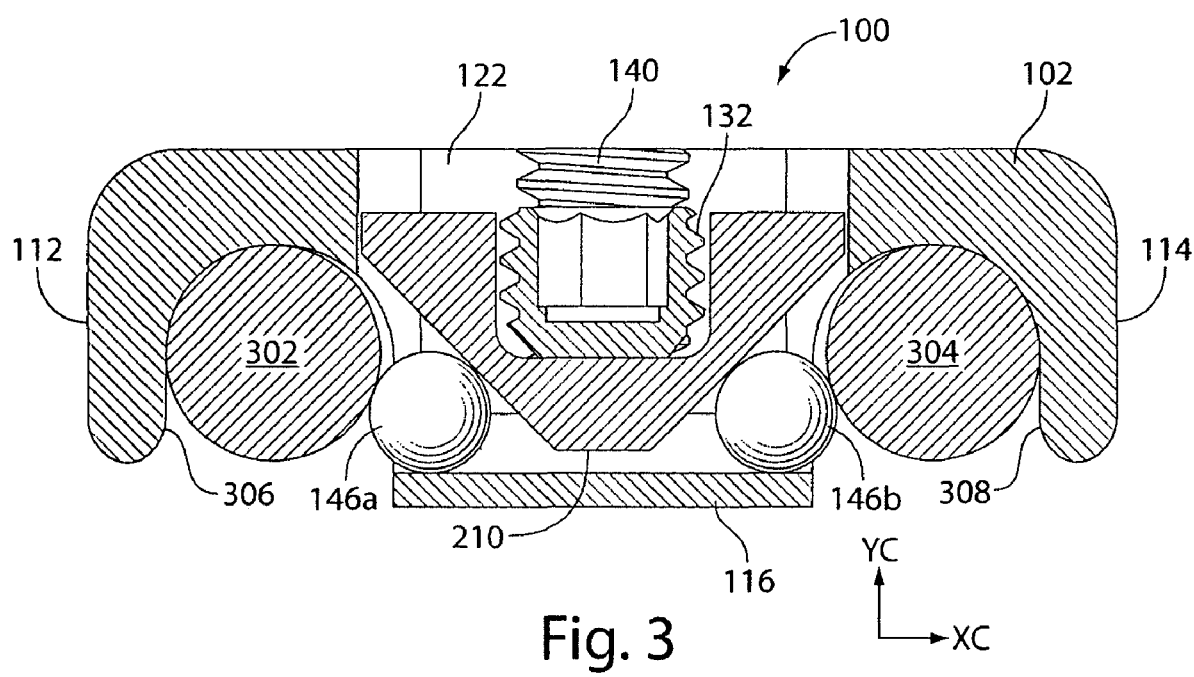
FIG. 3 illustrates a side, cross-sectional view of the embodiment show in FIGS. 1-2, of the present invention.
Figure 4:
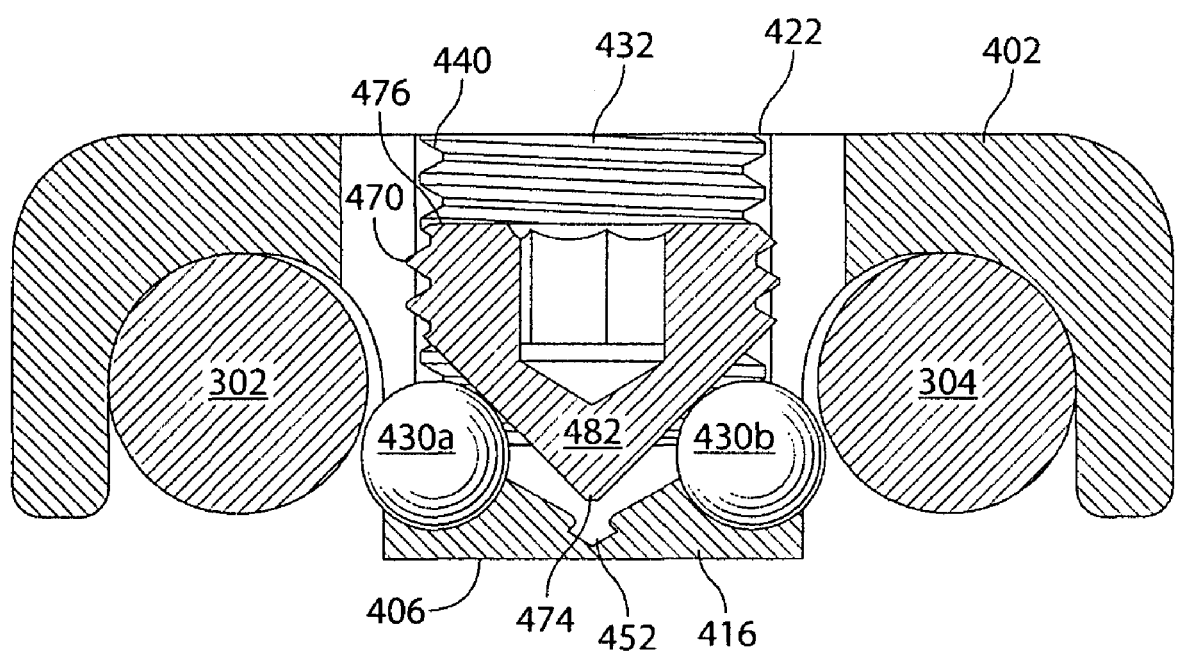
FIG. 4 illustrates a side, cross-sectional view of a lateral slot configuration according to another embodiment of the present invention (direct actuation without insert).

As shown, the opening 122 may be made in the top of the central portion 116 of the housing 102, and may be configured to accommodate insertion of spherical/circular objects/members 130a and 130b (not shown in FIG. 1), a setscrew 132, and an insert (FIGS. 2-4). The opening 122 may extend downward in the x-y plane, although preferably, in one embodiment, the depth of opening 122 may be less than the height of the housing 102 (see FIGS. 3-4). The opening 122 may further include threads 140 located longitudinally along the walls of the opening 122. Threads 140 are preferably configured to accommodate corresponding threads provided on an exterior portion of the setscrew 132, so that the setscrew 132 may be advanced into the opening 122.

The central portion 116 may further include openings 146a and 146b (not shown in FIG. 1). The openings 146 are made in the side walls of the central portion 116 that separate channels 118, 120 and the opening 122, respectively, and are preferably configured to allow spherical objects 130 to protrude into respective channels 118, 120, when the objects 130 are placed inside the opening 122. Once placed inside the opening 122, the opening and preferably the insert, direct spherical objects 130 to the openings 146, so that upon the objects 130 protruding out the openings, they interact with a respective rod.

FIG. 2 is an exploded perspective view of the connector 100. As shown in this embodiment, the setscrew 132 is configured to be placed inside an insert 210. The insert 210 is used to preferably apply equal pressure, developed by advancement of the setscrew into the opening 122 ("retaining force") to each of the spherical objects 130 when in contact with a respective rod. Accordingly, the combination of the spherical objects 130, the insert 210, and the setscrew 132 is then configured to correspond to the configuration of the opening 122.

In one embodiment, the spherical objects 130 are initially placed inside the opening 122, where each is positioned adjacent a respective opening 146, the insert 210 is placed on top of the spherical objects and, thereby, urges the spherical objects 130 closer to and/or out of the openings 146. The openings 146 are preferably configured to prevent the spherical objects 130 from falling out into the channels 118, 120, respectively. Once the insert 210 is placed inside the opening 122, the setscrew 132 is threaded into the opening 122. The threads 140 and corresponding threads 133 may be configured to allow clockwise or counter-clockwise advancement of the setscrew within opening 122. Various means known in the art to lock the setscrew within the opening 122 after it has been threaded therein. Moreover, as can also be understood by one skilled in the art, the setscrew 132 can using any advancement means for applying a force to insert (and/or objects 130), other then the use of screw threads.

In one embodiment, the insert 210 may have a trapezoidal shape, as shown in FIGS. 2 and 3, where the insert 210 may be further configured to have a length that is substantially equal to the larger diameter of the elliptical opening 122. The insert 210 may also have a width that is substantially equal to the shorter diameter of the elliptical opening 122. The insert 210 may also have a height that is substantially equal to the depth of the opening 122. In this way, the insert 210 may tightly fit inside the opening 122 and may be fixed inside the opening 122. The setscrew 132 along with the spherical objects 130 further prevents the insert 210 from becoming loose inside the opening 122.

As illustrated in FIGS. 2-4, the insert 210 may include a groove 214 sized to fit the setscrew 132. The groove 214 may be configured to have a cubical or a parallelepipedal shape in order to accommodate the cylindrical nature of the setscrew 132. As can be understood by one skilled in the art, the groove 214 can have any other shapes. The groove 214 is made in a longer base of the trapezoidal insert 210, as shown in FIG. 2, and may also be configured not to interfere with threads 140 on the housing 102.

The insert 210 further includes diagonal sides 218 (*a*, *b*) that are configured to contact the spherical objects 130 (*a*, *b*), respectively, when the insert 210 is placed inside the opening 122 on top of the spherical objects 130. In an embodiment, once the spherical objects 130, the insert 210, and the setscrew 132 are inserted into the opening 122, by applying a downward rotational force (along the y-axis) to the setscrew 132 (when screwing-in the setscrew 132), the setscrew 132 pushes the insert 210 down (along the y-axis) and thereby the sides 218 are pushed toward the spherical objects 130 (along the x-axis). Thus, the spherical objects 130 are pushed out from the openings 146 (along the x-axis).

Referring to FIG. 3, rods 302 and 304 are shown to be secured inside the channels 118, 120, respectively. This may be accomplished by placing the rods 302, 304 inside the channels 118, 120, placing a combination of the spherical objects 130, the insert 210 and the setscrew 132 inside the opening 122, and advancing the setscrew 132 along the threads 140. Accordingly, this results in the insert 210 being pushed downwards and applies a translational force along the x-axis on the spherical objects 130. Once, the spherical objects 130 are pushed out along the x-axis towards the rods 302 and 304, the rods 302, 304 are pushed towards inner walls 306, 308, respectively, of the housing 102. As can be seen in the figure, preferably, the spherical objects interact with the rods such that they force the rods into the channel (e.g., upwards and outwards). Thus, this arrangement secures or holds the rods 302 and 304 inside the housing 102.

FIG. 4 illustrates an alternate embodiment of the housing 402. In this embodiment, the housing 402 is substantially similar to the housing 102 of FIG. 1. However, instead of opening 102, the housing 402 includes an opening 422 that may have a circular shape and uniformly extend downward inside the central portion 416 of the housing 402 forming a cylindrical channel. Furthermore, the insert 482 may have an inverted conical-shape bottom 474 and a cylindrical top 476. The cylindrical top 476 may further include threads 470. Threads 470 are configured to interact with threads 440 placed on the inner walls of the opening 422.

In this embodiment, the opening 422 may also include a groove 452 located towards the bottom portion 406 of the housing 402 (the portions and sides of the housing 402 are similar to the housing 102 of FIG. 1). The groove 452 is configured to match the conical top 476 of the insert 482. As such, when the spherical objects 430 are placed inside the opening 422 and the insert 482 is placed inside the opening 422 and is advanced along threads 440, the sides of the conical bottom 474 contact the spherical objects 430 and push the spherical objects 430 along the x-axis, similar to the embodiment of FIG. 1. The groove 452 may be configured to receive the conical bottom 474 when the insert 482 is screwed-in along the threads 440.

In one embodiment, a setscrew 432 (similar to setscrew 132) can be threaded along the threads 440 inside the opening 422 to further secure the insert 482 and, thus, the rods 302 and 304. As can be understood by one skilled in the art, the setscrew 432 (or setscrew 132, if referring to FIG. 1) can be advanced or removed using a tool having a head configured to interact with a recess (for example) in the head of the setscrew (e.g., screwdriver, a hexagonal wrench).

As can be understood by one skilled in the art, the housing 102 can have any desired shape, such as cubical, parallelepipedal, spherical, elliptical, or any other shape. The housing 102 can also have rounded sides, portions and edges, as illustrated in FIG. 1. Additionally, the heights, widths, lengths of the side portion 112 or 114 can be same or different than the other and/or the height, width, length of the central portion 116.

As can be understood by one skilled in the art, the objects 130 can also have varying shapes and sizes, such as spheres, cubes, parallelepipeds, cylinders, or any other desired shapes. Further, the setscrew 132 can be any other locking device that is configured to secure the insert 210, the objects 130 and the rods 302, 304 inside the housing 102.

Example embodiments of the methods and components of the present invention have been described herein. As noted elsewhere, these example embodiments have been described for illustrative purposes only, and are intended to be limiting, and thus, other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A bone alignment rod connector, comprising:
   a housing having an opening configured to accommodate at least one rod; and
   a setscrew assembly having a setscrew, an insert configured to be placed inside the housing, and at least one spherical member, the insert includes at least one side configured to interact with the setscrew and the spherical member when the setscrew is inserted in the housing, wherein:
   the setscrew assembly is configured to secure the at least one rod when the at least one rod is placed in the opening; and
   upon insertion of the setscrew, the setscrew is configured to laterally push the at least one side of the insert towards the spherical member causing the spherical member to press against the at least one rod to secure the at least one rod inside the housing.

2. The bone alignment rod connector according to claim 1, wherein the housing further includes a pair of openings each configured to accommodate a rod.

3. The bone alignment rod connector according to claim 2, wherein the pair of openings each comprise a cylindrical shape.

4. The bone alignment rod connector according to claim 1, wherein the housing includes an opening in a top surface of the housing and wherein the setscrew is configured to be inserted through the opening in the top surface of the housing.

5. The bone alignment rod connector according to claim 4, wherein the opening in the top surface of the housing is further configured to accommodate placement of the insert configured to interact with the setscrew and the spherical member upon the setscrew being inserted.

6. The bone alignment rod connector according to claim 5, wherein the opening in the top surface includes a plurality of threads to correspond to a plurality of threads provided on an exterior of the setscrew.

7. The bone alignment rod connector according to claim 1, wherein the opening in the housing includes a diameter that is greater than a diameter of the at least one rod.

8. The bone alignment rod connector according to claim 1, wherein the insert is part of the setscrew having an inverted conical-shaped bottom.

9. The bone alignment rod connector according to claim 1, wherein the housing further includes a bottom portion configured to accommodate placement of the at least one rod.

10. The bone alignment rod connector according to claim 1, wherein the insert includes a groove sized to fit the setscrew.

11. The bone alignment rod connector according to claim 1, wherein the insert side includes a diagonal side configured to contact the at least one spherical member.

12. The bone alignment rod connector according to claim 1, wherein the insert includes an inverted conical-shaped bottom configured to contact the at least one spherical member.

13. A method for securing a bone alignment rod within a receiving portion of a housing, comprising:
providing a housing having a receiving portion for receiving a bone alignment rod, a setscrew, an insert configured to be placed inside the housing, a spherical member, wherein the insert includes at least one side configured to laterally push the at least one side of the insert towards the spherical member causing the spherical member to press against the receiving portion to secure the bone alignment rod inside the housing, and a top threaded opening configured to receive the setscrew and allow the setscrew to advance therein to establish a retaining force to retain the bone alignment rod within the receiving portion;
receiving the bone alignment rod within the receiving portion of the housing; and
advancing the setscrew into the threaded opening to establish the retaining force to retain the rod within the receiving portion.

14. The method according to claim 13, wherein the insert includes a diagonal side configured to contact the spherical member having a portion of which protrudes out an opening of the housing adjacent the receiving portion to apply the retaining force to retain the bone alignment rod within the receiving portion.

15. The method according to claim 13, wherein the insert side includes an inverted conical-shaped bottom configured to contact the spherical member having a portion of which protrudes out an opening of the housing adjacent the receiving portion to apply the retaining force to retain the bone alignment rod within the receiving portion.

16. A method for securing a spaced apart relationship between two bone alignment rods comprising:
providing a housing having a pair of receiving portions in a spaced apart arrangement and each for receiving a respective bone alignment rod, a setscrew, an insert configured to be placed inside the housing, a spherical member, wherein the insert includes at least one side configured to interact with the setscrew and the spherical member when the setscrew is inserted in the housing to laterally push the at least one side of the insert towards the spherical member causing the spherical member to press against at least one of the receiving portions to secure at least one of the bone alignment rod inside the housing, and a top threaded opening configured to receive the setscrew and allow the setscrew to advance therein to establish a retaining force to retain each bone alignment rod with a respective receiving portion;
receiving a respective bone alignment rod within each receiving portion of the housing; and
advancing the setscrew into the threaded opening to establish the retaining force to retain each bone alignment rod in a respective receiving portion.

17. The method according to claim 16, wherein the spherical member protrudes out of an opening in the housing adjacent a receiving portion to apply the retaining force to at least one bone alignment rod.

18. The method according to claim 16, wherein the insert includes diagonal sides configured to contact the spherical members, a respective spherical member having a portion thereof which protrudes out an opening of the housing adjacent a respective receiving portion for applying the retaining force to a respective bone alignment rod.

19. The method according to claim 16, wherein the insert side includes an inverted conical-shaped bottom configured to contact the spherical members, a respective spherical member having a portion thereof which protrudes out an opening of the housing adjacent a respective receiving portion for applying the retaining force to a respective bone alignment rod.

20. The method according to claim 16, wherein the insert is part of the setscrew.

* * * * *